United States Patent
Hayashi et al.

(10) Patent No.: US 6,252,095 B1
(45) Date of Patent: Jun. 26, 2001

(54) CATALYST FOR PARTIALLY OXIDIZING UNSATURATED HYDROCARBON

(75) Inventors: Toshio Hayashi, Kobe; Masahiro Wada, Nishinomiya; Masatake Haruta; Susumu Tsubota, both of Ikeda, all of (JP)

(73) Assignees: Director-General of Agency of Industrial Science and Technology, Tokyo; Nippon Shokubai Co., Ltd., Osaka, both of (JP)

( * ) Notice: Subject to any disclaimer, the term of this patent is extended or adjusted under 35 U.S.C. 154(b) by 0 days.

(21) Appl. No.: 09/403,643
(22) PCT Filed: Feb. 19, 1999
(86) PCT No.: PCT/JP99/00753
  § 371 Date: Oct. 22, 1999
  § 102(e) Date: Oct. 22, 1999
(87) PCT Pub. No.: WO99/43431
  PCT Pub. Date: Sep. 2, 1999

(30) Foreign Application Priority Data

Feb. 24, 1998 (JP) .................................................. 10/041833

(51) Int. Cl.⁷ .................................................. C07D 301/03
(52) U.S. Cl. .................................................. 549/523; 502/344
(58) Field of Search .............................. 502/344; 549/523

(56) References Cited

U.S. PATENT DOCUMENTS

| 3,923,843 | | 12/1975 | Wulff | 260/348.5 |
|---|---|---|---|---|
| 5,506,273 | * | 4/1996 | Haruta et al. | 518/713 |
| 5,550,093 | * | 8/1996 | Wan et al. | 502/74 |
| 5,623,090 | * | 4/1997 | Haruta et al. | 568/360 |
| 5,789,337 | * | 8/1998 | Haruta et al. | 502/334 |
| 5,859,265 | | 1/1999 | Muller et al. | 549/531 |
| 5,932,750 | * | 8/1999 | Hayashi et al. | 549/523 |
| 5,965,754 | * | 10/1999 | Clark et al. | 549/533 |
| 6,124,505 | * | 9/2000 | Haruta et al. | 568/360 |

FOREIGN PATENT DOCUMENTS

| 0709360A1 | 5/1996 | (EP) . |
|---|---|---|
| 0827779A1 | 3/1998 | (EP) . |
| 1339309 | 9/1971 | (GB) . |
| 53-039404 | 10/1978 | (JP) . |
| 07097378 | 4/1995 | (JP) . |
| 08127550 | 5/1996 | (JP) . |
| 9-256079 | 9/1997 | (JP) . |
| 10005590 | 1/1998 | (JP) . |
| 10-66870 | 3/1998 | (JP) . |
| 10-244156 | 9/1998 | (JP) . |
| 11-128743 | 5/1999 | (JP) . |

OTHER PUBLICATIONS

Supplementary European Search Report dated Nov. 10, 2000.

* cited by examiner

*Primary Examiner*—Tom Dunn
(74) *Attorney, Agent, or Firm*—Armstrong, Westerman, Hattori, McLeland & Naughton LLP

(57) ABSTRACT

This invention provides a catalyst for partial oxidation of unsaturated hydrocarbon, characterized in that the catalyst comprises finely divided gold particles immobilized on a titanium-containing oxide and is one subjected to a silylating treatment or a hydrophobilizing treatment. The catalyst of the invention shows little deactivation with time in a reaction for preparing an epoxide from unsaturated hydrocarbon, and can stably retain a high selectivity, a high activity and like excellent catalytic capability for a long term.

12 Claims, No Drawings

CATALYST FOR PARTIALLY OXIDIZING UNSATURATED HYDROCARBON

FIELD OF THE INVENTION

The present invention relates to a catalyst for partial oxidation of unsaturated hydrocarbon and a process for preparing an epoxide using said catalyst.

BACKGROUND ART

Methods industrially carried out for epoxidation generally employ chlorohydrin, organic peroxide, hydrogen peroxide or like oxidizing agents. However, these methods inevitably pose problems of requiring multi-stage reaction and generating by-products.

It is more convenient to convert unsaturated hydrocarbon to the corresponding epoxide using molecular oxygen as an oxidizing agent. However, this technique has been employed on an industrial scale only for the production of ethylene oxide from ethylene. The production of an epoxide from other unsaturated hydrocarbon, for example, propylene oxide directly from propylene by oxidation with oxygen, is very difficult to accomplish. Some methods for oxidation of propylene directly to propylene oxide with oxygen were proposed in publications (Japanese Examined Patent Publication No.39404/1978, Japanese Unexamined Patent Publication No.97378/1995, etc.). However, all of the proposed methods raise problems of low selectivity, low activity and other defects from the viewpoint of efficiency.

Proposed methods of producing an epoxide from unsaturated hydrocarbon with a high selectivity include methods comprising partially oxidizing unsaturated hydrocarbon in the presence of molecular hydrogen using a catalyst comprising gold and titanium oxide (Japanese Unexamined Patent Publications No. 127550/1996 and No.5590/1998). Yet, the proposed methods are problematic in that although active in some degree in the initial stage of reaction, the catalyst lowers its activity with time and shows an insufficient activity in a stationary state.

DISCLOSURE OF THE INVENTION

The present invention was accomplished to overcome the foregoing prior art problems. It is a principal object of the invention to provide a catalyst for partial oxidation of unsaturated hydrocarbon, the catalyst being useful in efficiently producing an epoxide from unsaturated hydrocarbon with a high selectivity and the catalyst being rarely deactivated with time and having a prolonged service life.

The inventors of the present invention carried out extensive research in view of the foregoing prior art problems, and found the following. When a catalyst comprises finely divided gold particles immobilized on a titanium-containing oxide and is subjected to a silylating treatment or a hydrophobilizing treatment, the catalyst can effectively exhibit its inherent properties depending on reaction conditions such as a reaction temperature and a reaction pressure in a reaction for preparing an epoxide from unsaturated hydrocarbon. Further, such catalyst hardly diminishes its activity with time and can stably retain a high selectivity, a high activity and like excellent catalytic capability for a long term. This invention was accomplished based on this novel finding.

According to the present invention, there are provided the following catalysts for partial oxidation of unsaturated hydrocarbon and a process for preparing an epoxide using the catalysts:

1. a catalyst for partial oxidation of unsaturated hydrocarbon, characterized in that the catalyst comprises finely divided gold particles immobilized on a titanium-containing oxide and is one subjected to a silylating treatment;
2. a catalyst for partial oxidation of unsaturated hydrocarbon, characterized in that the catalyst comprises finely divided gold particles immobilized on a titanium-containing oxide and is one subjected to a hydrophobilizing treatment;
3. the catalyst as defined in item 2, wherein the hydrophobilizing treatment is conducted using at least one hydrophobilizing agent selected from the group consisting of organic fluorinating agents and silylating agents;
4. the catalyst as defined in item 1 or 2, wherein the finely divided gold particles are ultra-fine particles having a particle size of 10 nm or less;
5. the catalyst as defined in item 1 or 2, wherein the titanium-containing oxide is at least one member selected from the group consisting of titanium oxides, titanates, oxide mixtures of titanium oxide and silicon-containing oxide physically mixed together, and composite oxides prepared by chemically bonding titanium and silicon via oxygen;
6. the catalyst as defined in item 1 or 2, wherein the titanium-containing oxide contains at least one element selected from the group consisting of alkali metals, alkaline earth metals, lanthanoids and thallium;
7. the catalyst as defined in item 1, wherein the silylating treatment is carried out by bringing the titanium-containing oxide into contact with a silylating agent at a temperature of 450° C. or lower before or after immobilizing the finely divided gold on the titanium-containing oxide;
8. the catalyst as defined in item 2, wherein the hydrophobilizing treatment is carried out by bringing the titanium-containing oxide into contact with a hydrophobilizing agent at a temperature of 450° C. or lower before or after immobilizing the finely divided gold on the titanium-containing oxide; and
9. a process for preparing an epoxide, characterized in that unsaturated hydrocarbon is partially oxidized with oxygen in the presence of the catalyst as defined in any of items 1–8 and molecular hydrogen.

The catalyst of the present invention comprises finely divided gold particles immobilized on a titanium-containing oxide, the catalyst being one subjected to a silylating treatment or a hydrophobilizing treatment.

Said catalysts are described below in more detail.

Titanium-containing Oxide

The titanium-containing oxide for use herein includes, for example, titanium oxides, titanates, oxide mixtures of titanium oxide and silicon-containing oxide physically mixed together (hereinafter referred to as "titanium-containing mixed oxide") and composite oxides prepared by chemically bonding titanium and silicon via oxygen (hereinafter referred to as "titanium-containing composite oxide"). These titanium-containing oxides can be used either alone or in combination. It is preferred to use a titanium-containing oxide having a large specific surface area. The shapes of the oxides are not limited, and include powders and other shapes of moldings.

Among the titanium-containing oxides, useful titanium oxides are not limited in respect of the crystalline structure, shape, size and the like, and include, for example, those having anatase-type structure, rutile-type structure or like crystal structure or having an amorphous structure. Preferred titanium oxides include those of anatase-type structure or amorphous structure and those having a relatively small primary particle size of about 10 to about 200 nm and a relatively large specific surface area of about 5 $m^2$/g or larger.

Examples of useful titanates are metal titanates such as $MgTiO_3$, $CaTiO_3$, $BaTiO_3$, $PbTiO_3$, $FeTiO_3$ and the like.

Among the titanium-containing mixed oxides and titanium-containing composite oxides, it is suitable to use those which are porous and which have a large specific surface area, preferably 1 m$^2$/g or larger, more preferably 50 to 1200 m$^2$/g.

Silicon-containing oxides to be used in the titanium-containing mixed oxide include, for example, amorphous silica; silicalite having crystal structure; silicon-containing oxide such as a metal silicate which comprises as a main component a silicon oxide; composite oxides comprising silicon and other metal, typical examples of the composite oxides being amorphous silica-alumina and zeolite which is crystal form of silica-alumina.

Useful titanium-containing composite oxides include (1) those having titanium oxide supported only on the surface of a silicon-containing oxide and (2) those having titanium existing inside the silicon-containing oxide as well as on the surface thereof. The titanium-containing composite oxides having titanium oxide supported only on the surface of a silicon-containing oxide as described above in item (1) are those with titanium supported in the form of titanium oxide having at least one $[TiO_4]^{4-}$ unit only on the surface of a silicon-containing oxide. The titanium oxide can exist in the crystal form such as anatase-type structure or rutile-type structure or in the amorphous structure. Useful silicon-containing oxides include those used in the titanium-containing mixed oxide.

There is no limitation on the state in which the titanium oxide is supported on the surface of a silicon-containing oxide insofar as it is in a state generally called "supported", e.g. chemically firmly bonded or immobilized through physical interaction, on the surface of a silicon-containing oxide.

There is no restriction on how to cause the titanium oxide to be supported on the surface of a silicon-containing oxide. Generally a titanium compound is adsorbed on or bonded to the surface of a silicon-containing oxide by methods such as immersion, ion exchange, chemical vapor deposition, etc. and is eventually caused to become stably supported thereon by calcination or the like. Titanium compounds for use in preparing titanium-containing composite oxides are suitably selected for use depending on the production process. Examples are titanium oxides; titanium alkoxides such as titanium methoxide, titanium ethoxide, titanium tetraisopropoxide, titanium tetra-n-butoxide, tetrakis(2-ethylhexyl)orthotitanate and the like; halogenated titanium compound such as titanium trichloride, titanium tetrachloride, titanium tribromide, titanium tetrabromide, titanium trifluoride, titanium tetrafluoride and the like; and titanium complexes containing organic compounds such as titanium bisammonium lactate dihydroxide, titanylacetyl acetonate, titanium diisopropoxide bisacetyl acetonate, titanocene dichloride and the like.

Examples of titanium oxides supported only on the surface of a silicon-containing oxide are a titanium oxide supported on the surface of amorphous silica, a titanium oxide supported on the surface of crystalline silicate such as silicalite or mesoporous silica (MCM-41, MCM-48, etc.), a titanium oxide supported on the surface of a composite oxide comprising at least two elements, such as silica-zirconia, silica-alumina and the like.

The composite oxide having titanium inside the silicon-containing oxide as well as on the surface thereof as described above in item (2) refers to the composite oxide having titanium as titanium oxide or titanium atoms inside the silicon-containing oxide as well as on the surface thereof. In the composite oxide, titanium exists in the form of an isolated $Ti^{4+}$ or an oxide having at least one $[TiO_4]^{4-}$ unit on the surface of a silicon-containing oxide and is present also inside thereof in the state that silicon atoms are substituted with titanium atoms. In this case, it is desirable that $Ti^{4+}$ or $[TiO_4]^{4-}$ be dispersed as highly as possible.

Such composite oxides can be prepared, e.g. by causing the precipitation of a titanium- and silicon-containing hydroxide mixture from a uniform solution containing a titanium compound and a silicon compound by methods such as co-precipitation or a sol-gel method, followed by calcining to eventually give an oxide. The silicon-containing oxide obtained by the foregoing method may be, for example, the same as the silicon-containing oxide in the titanium-containing mixed oxide. The titanium compound for use in this method is suitably selected according to the production process and the like from the same titanium compounds as used in the method described in item (1).

Specific examples of the composite oxide containing titanium in the form of an isolated $Ti^{4+}$ or an oxide having at least one $[TiO_4]^{4-}$ unit are titanium- and silicon-containing oxides prepared by a sol-gel method using alkoxy silane, titanium alkoxide and the like as raw materials or by a co-precipitation method using silica sol and titanium salt as raw materials; zeolite materials(X type, Y type, ZSM-5, ZSM-48, etc.) wherein aluminum is partly replaced with titanium and wherein titanium is incorporated in the zeolite lattice; materials wherein mesoporous silica having large mesopores (MCM-41, MCM-48, MCM-50, etc.) is partly replaced with titanium atoms; microporous titanosilicate (so-called TS-1 or TS-2) which is a titanium-silicon composite oxide; and the like.

The proportion of the titanium in the titanium-containing mixed oxide and titanium-containing composite oxide is in the range of preferably 0.1/100 to 50/100, more preferably 0.5/100 to 20/100, calculated as the Ti/Si atom ratio (hereinafter referred to as "Ti/Si"). If the proportion of the titanium is less than Ti/Si=0.1/100, the catalyst exhibits the same degree of catalytic capability as a catalyst comprising a silica support alone, and selective oxidation of hydrocarbon does not occur. Hence the proportion of titanium lower than said range is undesirable.

Said titanium-containing oxide may further contain at least one element selected from the group consisting of alkali metals, alkaline earth metals, lanthanoids and thallium. The titanium-containing oxide containing these elements sometimes shows higher catalytic capability and tends to increase the service life stability of a catalyst. Useful alkali metals are, for example, Li, Na, K, Rb, Cs, Fr and the like. Usable alkaline earth metals include Be, Mg, Ca, Sr, Ba, Ra and the like. Among them, it is desirable to use component(s) selected from alkali metals such as Na, K, Rb and Cs and from alkaline earth metals such as Mg, Ca, Sr and Ba. Usable as lanthanoids are La, Ce, Sm and the like.

At least one element selected from the group consisting of alkali metals, alkaline earth metals, lanthanoids and thallium exists as a cation in the titanium-containing oxide and may be present on the surface of the titanium-containing oxide or may be incorporated in the crystals or inside the oxide.

The amount of at least one element selected from the group consisting of alkali metals, alkaline earth metals, lanthanoids and thallium in the titanium-containing oxide is preferably 0.001 to 20% by weight, more preferably 0.005 to 5% by weight, most preferably 0.01 to 2% by weight, based on the weight of the titanium-containing oxide. When the titanium-containing oxide contains a titanate such as $MgTiO_3$, $CaTiO_3$, $BaTiO_3$, etc., at least one element selected from the group consisting of alkali metals, alkaline earth metals, lanthanoids and thallium can be contained in the oxide in more amount, specifically in an amount of preferably about 0.1 to about 50% by weight, based on the weight of the titanium-containing oxide.

Said titanim-containing oxides can be used as immobilized on a molded carrier to further increase the catalytic activity. Useful carriers are titanium-free materials composed of metallic oxides, various kinds of metals, or the like. Examples are ceramics prepared from alumina (aluminum oxide: $Al_2O_3$), silica (silicon dioxide: $SiO_2$), magnesia (magnesium oxide: MgO), cordierite, zirconium oxide, composite oxides thereof or the like; foamed products prepared from metals, honeycomb carriers made from metals, pellets of metals, etc.

Preferred carriers are those containing at least one member selected from alumina and silica. Among them, those containing silica are more preferred. The term "those containing at least one member selected from alumina and silica" is used herein to include carriers containing zeolite (aluminosilicate) or silica-alumina.

There is no restriction on the foregoing carriers with respect to the crystalline structure, shape, size and the like. However, useful carriers are those having a specific surface area of preferably 50 $m^2/g$ or more, more preferably 100 $m^2/g$ or more. In the case of a specific surface area of 50 $m^2/g$ or more, side reactions such as successive oxidation can be more inhibited, resulting in efficient partial oxidation of unsaturated hydrocarbon and in increased catalytic capability.

When the titanium-containing oxide is used as immobilized on a carrier, a preferred amount of the titanium-containing oxide to be used is about 0.5 to about 20% by weight based on the carrier. The titanium-containing oxide is caused to be supported on a carrier such as silica, alumina or the like, e.g. by a sol-gel method using alkoxide, a kneading method, a coating method or the like. According to these methods, the titanium-containing oxide can be supported as dispersed on the carrier to provide the so-called island structure.

Immobilization of Finely Divided Gold Particles

In the present invention, it is required to immobilize the finely divided gold particles on said titanium-containing oxide. The gold for use herein is preferably in the form of ultra-fine particles having a particle size of 10 nm (nanometer) or less. Such ultra-fine gold particles are supported as firmly immobilized on the titanium-containing oxide serving as a support, whereby the catalytic activity is especially improved.

The proportion of gold to be supported is preferably at least 0.001% by weight, more preferably 0.01% to 20% by weight, most preferably 0.05 to 10% by weight, based on the titanium-containing oxide. If the proportion of gold supported on the oxide is less than 0.001% by weight, the catalytic activity is insufficient. Hence, it is undesirable. On the other hand, even if the proportion of gold supported on the oxide is more than 20% by weight, the catalytic activity is not more improved than in said proportion range. The surfeit of gold is of no use and hence it is undesirable.

Methods of immobilizing the finely divided gold particles on a titanium-containing oxide are not limited insofar as they can stably fix the gold particles on the titanium-containing oxide.

Specific examples of methods of immobilizing finely divided gold particles on the titanium-containing oxide include precipitation methods in accordance with the process for preparing a titanium-containing metal oxide with finely divided gold particles immobilized thereon as disclosed in Japanese Unexamined Patent Publication No.8797/1995. The methods are briefly described below.

(1) First Process

A solution containing a titanium-containing oxide is adjusted to a pH of 7–11, preferably 7.5 to 10. Then an aqueous solution of a gold compound is added dropwise to the solution with stirring to precipitate gold hydroxide on the titanium-containing oxide. The titanium-containing oxide with the gold hydroxide precipitated thereon is heated to a temperature of 100 to 800° C., whereby the finely divided gold particles are deposited on the titanium-containing oxide and are immobilized thereon.

The amount of the titanium-containing oxide to be added to water is not limited. For example, when a powdery titanium-containing oxide is used, its amount is in a range sufficient to uniformly disperse or suspend the titanium-containing oxide in water, suitably in a range of about 10 to about 200 g/l. Further, when the titanium-containing oxide is used as a molded product, the amount of titanim-containing oxide is not limited insofar as the aqueous solution can be sufficiently contacted with the surface of molded product according to the shape of molded product.

Gold compounds to be used in the form of an aqueous solution are, for example, chloroauric acid ($HAuCl_4$), sodium chloroaurate ($NaAuCl_4$), gold cyanide (AuCN), potassium cyanoaurate $\{K[Au(CN)_2]\}$, trichlorodiethylamineauric acid $[(C_2H_5)_2NH.AuCl_3]$ and like water-soluble gold salts. There is no limitation on the concentration of the gold compound in the aqueous solution to be added dropwise. A suitable concentration is in the range of about 0.1 to about 0.001 mol/l.

An alkali compound such as sodium carbonate, sodium hydroxide, potassium carbonate or ammonia is usually used to adjust a dispersion or a suspension containing the titanium-containing oxide to a specified pH range.

The aqueous solution of a gold compound is preferably gradually added dropwise with stirring to said dispersion or suspension to prevent excessive precipitation of gold hydroxide due to abrupt reaction. Usually the time of dropwise addition is in the range of about 3 to about 60 minutes depending on the amount of the aqueous solution to be added dropwise. And the rate of dropwise addition is suitably controlled to avert the excessive precipitation of gold hydroxide.

A suitable temperature of the solution containing the titanium-containing oxide at the time of dropwise addition is in the range of about 20 to about 80° C.

The amount of the aqueous solution of gold compound to be added dropwise is determinable according to the amount of ultra-fine gold particles to be supported on the titanium-containing oxide.

When the titanium-containing oxide having gold hydroxide precipitated thereon is heated to a temperature of 100 to 800° C., the gold hydroxide is decomposed, whereby gold is uniformly deposited as ultra-fine particles on the titanium-containing oxide and is firmly immobilized thereon. The heating time is usually about 1 to about 24 hours.

The gold hydroxide can also be precipitated on the titanium-containing oxide by adding the titanium-containing oxide to the aqueous solution of gold compound instead of adding dropwise the aqueous solution of gold compound to the solution containing the titanium-containing oxide.

According to this method, an aqueous solution of gold compound is heated with stirring to a temperature of 30 to 100° C., preferably 50 to 95° C. and is adjusted to a pH of 6–12, preferably 7–10 using an aqueous alkaline solution, followed by addition of titanium-containing oxide at one time or by gradual addition thereof over a few minutes. In this method, if the pH is varied, stirring is continued at the same temperature while retaining the pH at 6–12, preferably 7–10 with the use of the alkaline solution.

The amount of the aqueous solution of gold compound and the concentration of gold compound in the aqueous solution are not limited and determinable according to the amount of titanium-containing oxide to be used and the amount of gold particles to be supported on the titanium-containing oxide. A suitable concentration of gold compound is about 0.0001 to about 0.01 mol/l.

The titanium-containing oxide can be added as such or as dispersed or suspended in water in a suitable concentration to the aqueous solution of gold compound. The amount of titanium-containing oxide to be used is not limitative. For example, when a powdery titanium-containing oxide is used, the amount may be in the range sufficient to uniformly disperse or suspend the titanium-containing oxide in water. Usually a suitable amount of titanium-containing oxide in the aqueous solution is about 10 to about 200 g/l. If the titanium-containing oxide is used as a molded product, the amount of titanium-containing oxide is unlimited insofar as the aqueous solution can be sufficiently contacted with the surface of the molded product depending on the shape thereof.

The gold compound, titanium-containing oxide, alkali compound for adjustment of pH and the like may be the same as used in the method of adding dropwise the aqueous solution of gold compound to the dispersion or suspension of titanium-containing oxide.

When required, the titanium-containing oxide having gold hydroxide precipitated thereon by such a method may be washed with water and separated by filtration or like methods. Then the titanium-containing oxide is heated to a temperature of about 100 to about 800° C. in the same manner as above, giving the titanium-containing oxide with the ultra-fine gold particles immobilized thereon.

The gold hydroxide can be precipitated on the titanium-containing oxide also by a combination of the foregoing two methods. For example, the gold compound and the titanium-containing oxide can be added to water simultaneously or alternately. In this case, the concentration of the solution, its pH, its temperature and the like can be suitably determined over the ranges under the conditions of two methods. The thus obtained titanium-containing oxide with gold hydroxide precipitated thereon is heated to a temperature of about 100 to about 800° C., whereby the ultra-fine gold particles can be immobilized thereon.

(II) Second Method

An aqueous solution of a reducing agent is added dropwise with stirring to an aqueous solution containing a gold compound and a titanium-containing oxide with a pH of 7 to 11 (preferably 7.5 to 10) to deposit ultra-fine gold particles due to reduction on the surface of titanium-containing oxide and to immobilize them on its surface.

As to the gold compound, the titanium-containing oxide and the pH-adjusting alkali compound, the same species exemplified above for the first method may be used in the second method. The amount of the titanium-containing oxide to be used in the second method may be the same as in the first method. The concentration of gold compound in the solution in the second method is suitably about $1 \times 10^{-2}$ to about $1 \times 10^{-5}$ mol/l. A proper temperature of the aqueous solution containing the titanium-containing oxide is 0 to about 80° C. at the time of reaction.

Examples of useful reducing agents are hydrazine, formalin, sodium citrate and the like. The concentration of the reducing agent in the solution is about $1 \times 10^{-1}$ to about $1 \times 10^{-3}$ mol/l. A suitable amount of the aqueous solution of the reducing agent to be used is about 1.5 to about 10 times the stoichiometric amount. It is desirable that the aqueous solution of the reducing agent be gradually added dropwise to avert abrupt deposition of gold from the reaction mixture. The dropwise addition is carried out usually over a period of about 3 to about 60 minutes.

The obtained titanium-containing oxide having ultra-fine gold particles immobilized thereon can be used as such at room temperature. However, when used at a high temperature, the titanium-containing oxide is desirably heated before use to almost the same temperature as during use to assure the stability of the catalyst at a high temperature.

(III) Third Method

A carbon dioxide gas is blown into an aqueous solution containing a gold compound and a titanium-containing oxide and having a pH of at least 11 (preferably 11 to 12) or an acidic aqueous solution is gradually added dropwise with stirring to the aqueous solution to decrease the pH to 7–11, thereby precipitating gold hydroxide on the surface of a titanium-containing oxide. Thereafter the titanium-containing oxide is heated to a temperature of 100 to 800° C. to deposit ultra-fine gold particles on the surface of titanim-containing oxide.

As to the gold compound, the titanium-containing oxide and the alkali compound, the same amounts of the same species as used in the first method may be used in the third method. The solution containing a titanium-containing oxide is used at a temperature of about 20 to about 80° C.

In the third method, the gold compound is required to remain dissolved as complex ions having hydroxyl group excessively bonded thereto in the aqueous solution containing the titanium-containing oxide. Therefore, the pH of the aqueous solution containing the titanium-containing oxide is controlled in the range of at least 11 such that the gold compound is dissolved as hydroxyl-containing complex ions according to the gold compound to be used.

A carbon dioxide gas is blown into the aqueous solution so adjusted or alternatively an acidic aqueous solution is gradually added dropwise to the aqueous solution to slowly lower the pH of the solution to 7–11, whereby gold hydroxide is precipitated on the surface of titanium-containing oxide as a core and adheres thereto.

The rate of blowing a carbon dioxide gas is unlimited insofar as it is in the range wherein the reaction mixture is uniformly bubbled.

Usable as acidic solutions are, for example, aqueous solutions of nitric acid, hydrochloric acid, sulfuric acid, acetic acid and the like. These acidic aqueous solutions can be used in a concentration of about $1 \times 10^{-1}$ to about $1 \times 10^{-3}$ mol/l. The amount of the acidic solution to be added dropwise is in the range wherein the solution containing the titanium-containing oxide is not brought to a pH of less than 7. The rate of dropwise addition is suitably determined according to the amount of the solution to be added dropwise in consideration of the time of dropwise addition ranging from about 3 to about 60 minutes to avoid excessive precipitation of gold hydroxide.

The titanium-containing oxide having the gold hydroxide precipitated thereon is heated to a temperature of 100 to 800° C., whereby the gold hydroxide is decomposed, and the gold is uniformly deposited as ultra-fine particles over the titanium-containing oxide and is firmly immobilized thereon. The heating time is usually about 1 to about 24 hours.

It is preferred in any of said methods to stir the aqueous solution containing the titanium-containing oxide for about 30 minutes to about 2 hours after dropwise addition of the solution or after blowing a carbon dioxide gas so as to sufficiently precipitate the gold compound on the titanium-containing oxide.

The catalyst for use in this invention can be prepared also according to the method as disclosed in Japanese Unexamined Patent Publication No.122478/1997 for preparing a aterial having ultra-fine gold particles immobilized thereon using a vapor of organic gold complex. The disclosed method is briefly described below.

In this method, vaporized organic gold complex is adsorbed on a titanium-containing oxide under reduced pressure and heated to a temperature of 100 to 700° C., giving a titanium-containing oxide having ultra-fine gold particles immobilized thereon.

Useful organic gold complexes are not limited insofar as they are volatile. For example, use is made of at least one of $(CH_3)_2Au(CH_3COCHCOCH_3)$, $(CH_3)_2Au(CF_3COCHCOCH_3)$, $(CH_3)_2Au(CF_3COCHCOCF_3)$, $(C_2H_5)_2Au(CH_3COCHCOCH_3)$, $(CH_3)_2Au(C_6H_5COCHCOCF_3)$, $CH_3CH_2AuP(CH_3)_3$ and $CH_3AuP(CH_3)_3$.

Before adsorption of vaporized organic gold complex, the titanium-containing oxide may be heat-treated at about 200° C. to remove water or the like from its surface.

The organic gold complex can be vaporized usually at a temperature of 0 to about 90° C. In the case of heating, preferably the heating temperature is determined over a range which will not cause abrupt vaporization, adsorption, or decomposition. The vaporization can also be effected under reduced pressure ranging from about $1 \times 10^{-4}$ to about $2 \times 10^{-3}$ Torr.

The vaporized organic gold complex is adsorbed on a titanium-containing oxide under reduced pressure. The term "under reduced pressure" used herein refers to a pressure below the atmospheric pressure and properly a pressure in the range of usually about $1 \times 10^{-4}$ to about 200 Torr. The amount of the organic gold complex to be used is variable depending on the type of gold complex to be used and is suitably adjusted to a range which will finally realize the foregoing amount of immobilized gold. The pressure may be adjusted by a conventional vacuum pump or the like.

Subsequently the titanium-containing oxide having the organic gold complex adsorbed thereon is heated in air at a temperature of about 100 to about 700° C., preferably about 300 to about 500° C. Thereby the organic component in the organic gold complex is decomposed and oxidized, and the organic gold complex is reduced to gold, which is then deposited as ultra-fine particles on the titanium-containing oxide and immobilized thereon. The heating time can be suitably determined according to the amount of the organic gold complex adsorbed on the titanium-containing oxide, heating temperature, etc. It is usually in the range of about 1 to about 24 hours. In this way, a titanium-containing oxide having ultra-fine gold particles immobilized thereon is obtained.

In the foregoing method, the titanium-containing oxide can be surface-treated by heating usually at about 100 to about 700° C. before adsorption of organic gold complex. The surface treatment can be effected in the atmosphere of oxidizing gas or reducing gas. Thereby the amount of defective portion and the state on the surface of titanium-containing oxide are more easily controlled, and the particle size and the amount of gold particles to be supported can be more finely controlled.

Useful oxidizing gases include conventional ones such as oxygen gas, nitrogen monoxide gas, etc. Useful reducing gases include conventional ones such as hydrogen gas, carbon monoxide gas, etc.

According to the gold-precipitating methods and the organic gold complex-vaporizing method described above, ultra-fine gold particles can be firmly immobilized on the titanium-containing oxide in a relatively uniform distribution.

When said catalyst is used as supported on a carrier, a suitable method comprises causing a titanium-containing oxide to be supported on a carrier and then immobilizing gold particles on the oxide. To immobilize gold on the titanium-containing oxide supported on a carrier, a carrier having the titanium-containing oxide supported thereon is used in place of the titanium-containing oxide in the gold-precipitating methods and the organic gold complex-vaporizing method described above. The gold-precipitating methods are advantageous in that ultra-fine gold particles are immobilized only on the titanium-containing oxide (especially in the position of titanium ions) while being scarcely deposited on the carrier. When a carrier consisting of or containing silica is used, the gold-precipitating methods are pronouncedly advantageous in that ultra-fine gold particles can be immobilized only on the titanium-containing oxide with an especially high selectivity.

Silylating Treatment

The silylating treatment can be carried out by bringing a titanium-containing oxide into contact with a silylating agent at an optional time before or after immobilization of gold particles on the titanium-containing oxide. More specifically, the titanium-containing oxide is contacted with a silylating agent after immobilization of gold particles on the titanium-containing oxide, or the gold particles are immobilized on the titanium-containing oxide by any of the foregoing methods after contact of a silylating agent with the titanium-containing oxide.

The silylating treatment is capable of pronouncedly reducing the accumulation of a high-boiling organic substance on the surface of a catalyst, the accumulation being presumably responsible for the catalyst deactivation. The treatment can alleviate the deactivation with time and can bring about the inherent performances of the catalyst according to the reaction conditions such as a reaction temperature, a reaction pressure and the like.

Examples of the silylating agent to be used are organosilane, organosilylamine, organosilazane, and the like. Specific examples of the organosilane are chlorotrimethylsilane, dichlorodimethylsilane, chlorobromodimethylsilane, nitrotrimethylsilane, chlorotriethylsilane, chlorodimethylphenylsilane, dimethylpropylchlorosilane, dimethyloctylchlorosilane, tributylchlorosilane, dimethoxymethylchlorosilane, methoxytrimethylsilane, dimethoxydimethylsilane, methyltrimethoxysilane, dimethoxydiphenylsilane, trimethoxyphenylsilane, ethoxytrimethylsilane, ethyltrimethoxysilane, diethoxydimethylsilane, diethoxydiethylsilane, ethyltriethoxysilane, trimethylisopropoxysilane, methoxytripropylsilane, butyltrimethoxysilane, octyltrimethoxysilane, acetoxytrimethylsilane, etc. Specific examples of the organosilylamine are dimethylaminotrimethylsilane, diethylaminotrimethylsilane, N-trimethylsilyldimethylamine, bis(dimethylamino) dimethylsilane, methylsilatrane, N-trimethylsilylimidazole, N-trimethylsilylpyrrolidine, etc. Specific examples of the organosilazane are haxamethyldisilazane, heptamethyldisilazane, 1,1,3,3-tetramethyldisilazane, 1,3-diphenyltetramethyldisilazane, etc. Specific examples of other silylating agents are tetramethoxysilane, tetraethoxysilane, 3-aminopropyltrimethoxysilane, 3-cyanopropyltrichlorosilane, 2-cyanoethyltrimethoxysilane, mercaptomethyltrimethoxysilane, dimethoxy-3-mercaptopropylmethylsilane, 3-mercaptopropyltrimethoxysilane, 3,3,4,4,5,5,6,6,6-nonafluorohexyltrichlorosilane, trimethylsilyltrifluoromethane sulfonate, N,O-bistrimethylsilylacetamide, N-trimethylsilylacetamide, N,N'-bistrimethylsilyl urea, etc. These silylating agents can be used either alone or in combination.

The silylating agent can be used in the form of either a liquid or a gas. Preferably the silylating agent is held at a temperature of 450° C. or lower when contacted with a titanium-containing oxide. The silylating treatment is conducted, for example, by mixing the titanium-containing oxide and a liquid silylating agent, and heating the mixture, or by contacting a vapor of silylating agent with the titanium-containing oxide heated to a suitable temperature. Useful liquid silylating agents include those available as a liquid product, and those containing silylating agent(s) as dissolved in a suitable solvent. Useful solvents are, for example, alcohols, ketones, ethers, esters, hydrocarbons, etc. More specific examples are methanol, 2-propanol, acetone, methyl ethyl ketone, diisopropyl ether, tetrahydrofuran, ethyl acetate, butyl acetate, toluene, xylene, etc. A preferred concentration of the silylating agent in the solution is about 0.01 to about 1 mol/l. The silylating treatment can be performed by any of batchwise method, semi-batchwise method and continuous method.

A silylating temperature is preferably −20 to 450° C., more preferably −10 to 420° C., most preferably 0 to 400° C. If the silylating temperature is higher than 450° C., the silylation fails to fully improve a catalytic capability for catalytic reaction or to sufficiently alleviate the degradation of catalytic capability with time. Hence it is undesirable. The silylating time is variable depending on the silylating agent to be used, silylating temperature and other factors. Generally a suitable silylating time is about 0.1 second to about 2 hours at a silylating temperature of 0 to about 400° C.

A suitable amount of the silylating agent to be used, although widely variable, is about 0.01 to about 100 parts by weight, preferably about 0.1 to about 10 parts by weight, per 100 parts by weight of the titanium-containing oxide.

If the extent of silylating treatment is insufficient, the catalytic capability would not be fully improved. On the other hand, when an excessive degree of silylating treatment is done, the surface of catalyst is covered with silyl group, resulting in lower catalytic activity. Consequently proper silylating conditions should be selected from the foregoing ones according to the kind of catalyst to be used and reaction condition.

According to silylating methods using an organic silylating agent, the organic silylating agent is reacted with OH group in silanol group or like on the surface of the catalyst to thereby bring about organosilylation. During the silylation, the OH group is decreased, leading to a change in inherent acidity-basicity of catalyst, especially to a decrease in strong acid sites. Presumably the life stability of the catalyst and hydrogen efficiency are thereby further improved.

The thus silylated catalyst can be qualitatively analyzed by optical means such as infrared spectrophotometric analysis. For example, a gold-titania-silica catalyst shows increased peaks of CH vibration in the vicinity of 2970 cm$^{-1}$ with the progress of organosilylation and indicates decreased peaks of OH vibration in the vicinity of 3750 cm$^{-1}$.

When gold and a titanium-containing oxide to be silylated are subjected to hydration treatment before the silylation, the silylation efficiency (silylating degree) may be effectively enhanced. The hydration treatment can be conducted before the silylation, e.g. by contact of the catalyst with water and heating the hydrated catalyst or by contact of the catalyst with a water vapor at about 150 to about 450° C. for about 0.1 to about 2 hours.

Hydrophobilizing Treatment

The hydrophobilizing treatment is done to lower the water absorption of a catalyst having finely divided gold particles immobilized on a titanium-containing oxide.

The hydrophobicity of the catalyst is evaluated in terms of the hydrophobilizing degree given by an equation shown below using a ratio of the water absorptions of the catalyst before and after hydrophobilizing treatment. It is desirable in this invention that the hydrophobilizing degree be 10–98%, preferably 20–95%, more preferably 30–90%. The water absorption can be measured by conventional methods such as standardized methods of measuring the water absorption, inclusive of silica gel test methods (as specified by JIS), thermogravimetric analysis (TG), temperature programmed desorption(TPD), etc.

Hydrophobilizing degree $(W_p)$ $(\%)=100(A_0-A_r)/A_0$ $A_0$: water absorption of the catalyst before hydrophobilizing treatment $A_r$: water absorption of the catalyst after hydrophobilizing treatment.

Water absorption (A) $(\%)=100(W_0-W)/W$

W: weight (g) of a dried sample $W_0$: weight (g) of a sample containing absorbed water.

The hydrophobilizing treatment according to this invention can be conducted, for example, by two types of methods which follow.

(1) A first method is a method of hydrophobilizing treatment using a hydrophobilizing agent.

Hydrophobilizing agents useful herein are not limited and include organic fluorinating agents and the like. Examples of useful organic fluorinating agents are fluorine-containing polymeric compounds such as polytetrafluoroethylene, polyvinylidenefluoride and the like, and fluorine-containing compounds such as trifluoromethyl alcohol, trifluoroacetic acid, trifluoromethyl ethylene oxide and the like.

The water absorption as measured after silylation is sometimes lower due to silylation than before silylation. This shows that the silylating agent acted as a hydrophobilizing agent.

Useful hydrophobilizing agents can be used either alone or in combination.

The hydrophobilizing treatment can be performed at an optional time before or after immobilization of gold particles on a titanium-containing oxide. More specifically, a hydrophobilized catalyst can be obtained either by contact of a titanium-containing oxide with a hydrophobilizing agent after immobilization of gold particles on the titanium-containing oxide, or by immobilization of gold particles on a titanium-containing oxide by any of the foregoing methods after hydrophobilizing treatment by contact of a hydrophobilizing agent with the titanium-containing oxide.

The hydrophobilizing treatment is capable of pronouncedly reducing the accumulation of a high-boiling organic substance on the surface of catalyst, the accumulation being considered responsible for the degradation of catalytic capability. The treatment not only can alleviate the impairment of catalytic capability with time but also can cause the catalyst to effectively exhibit its inherent catalytic capability according to reaction conditions such as a reaction temperature, a reaction pressure and the like.

The hydrophobilizing agent can be used in the form of either a liquid or a gas. Preferably the hydrophobilizing agent is held at a temperature of 450° C. or lower when contacted with the titanium-containing oxide. For example, the hydrophobilizing treatment is conducted by mixing the titanium-containing oxide and a liquid hydrophobilizing agent and heating them, or by contacting a vapor of hydrophobilizing agent with the titanium-containing oxide heated to a suitable temperature. Useful liquid hydrophobilizing agents include those available as a liquid product and those containing hydrophobilizing agent(s) as dissolved in a suitable solvent. Useful solvents are, for example, alcohols, ketones, ethers, esters, hydrocarbons, etc. More specific examples are methanol, 2-propanol, acetone, methyl ethyl ketone, diisopropyl ether, tetrahydrofuran, ethyl acetate, butyl acetate, toluene, xylene, etc. A preferred concentration of the hydrophobilizing agent in the solution is about 0.01 to about 1 mol/l. The hydrophobilizing treatment can be performed by any of batchwise method, semi-batchwise method and continuous method.

A hydrophobilizing temperature is preferably −20 to 450° C., more preferably −10 to 420° C., most preferably 0 to 400° C. If the hydrophobilizing temperature is higher than 450° C., the hydrophobilization fails to fully improve a catalytic capability for catalytic reaction and to sufficiently alleviate the degradation of catalytic capability with time. Hence it is undesirable. The hydrophobilizing time is variable depending on the hydrophobilizing agent to be used, hydrophobilizing temperature and other factors. Generally a suitable hydrophobilizing time is about 0.1 second to about 2 hours at a hydrophobilizing temperature of 0 to about 400° C.

A suitable amount of the hydrophobilizing agent to be used, although variable over a wide range, is about 0.01 to about 100 parts by weight, preferably about 0.1 to about 10 parts by weight, per 100 parts by weight of the titanium-containing oxide.

When the extent of hydrophobilizing treatment is insufficient, the catalytic capability can not be fully improved. On the other hand, when an excessive degree of hydrophobilizing treatment is done, the surface of the catalyst is covered, resulting in lower catalytic activity. Consequently proper hydrophobilizing conditions should be selected from the foregoing ones according to the kind of catalyst to be used, reaction conditions, etc.

According to hydrophobilizing methods using an organic fluorinating agent, the reagent may be reacted with OH group in silanol group or like on the surface of the catalyst to bring about organic fluorination. In this case, the OH group is decreased, thereby leading to a change in inherent acidity-basicity of the catalyst, especially to an additional advantage of a decrease in strong acid sites. Presumably the life stability of the catalyst and hydrogen efficiency may be thereby further improved.

When gold and a titanium-containing oxide to be hydrophobilized are subjected to hydration treatment before the hydrophobilizing treatment, the hydrophobilizing efficiency (hydrophobilizing degree) may be increased. The hydration treatment can be conducted, e.g. by contacting the catalyst with water and heating the hydrated catalyst before hydrophobilization or by contacting the catalyst with a water vapor at about 150 to about 450° C. for about 0.1 to about 2 hours before hydrophobilization.

(2) A second method includes, for example, a method wherein finely divided gold particles and a titanium-containing oxide are immobilized on the surface of a hydrophobic substance, and a method wherein a hydrophobic substance is physically mixed with gold particles and a titanium-containing oxide. Useful hydrophobic substances are not limited insofar as they are capable of attaining a hydrophobilizing degree in a positive range. Examples are fluorine-containing polymers, hydrocarbon-based polymers, activated carbon, hydrophobic silica, high-silica zeolite.

Useful fluorine-containing polymers are, for example, those composed of fluorine-containing hydrocarbon, typical examples being porous polytetrafluoroethylene (Teflon), polyvinylidenefluoride and the like. Useful hydrocarbon-based polymers include styrene-divinylbenzene copolymers, polypropylene, etc. Useful hydrophobic silicas include commercially available silicas such as AEROSIL R812 (trade name for hydrophobic silica manufactured by Nihon Aerosil Co., Ltd.). Useful high-silica zeolites include those having MFI structure such as silicalite, MCM-41 and the like; Si- and Al-containing zeolite treated with an acid to reduce the Al content; etc.

There is no limitation on the method of immobilizing gold particles and a titanium-containing oxide on the surface of a hydrophobic substance. Useful methods include a method comprising immobilizing a titanium-containing oxide on the surface of a hydrophobic substance and then immobilizing gold particles thereon, a method comprising immobilizing gold particles on a titanium-containing oxide and then immobilizing them on a hydrophobic substance, etc. The term "immobilizing" used herein means not only chemically firmly bonding but bonding through mechanically or physically weak interaction.

There is no restriction on the method of physically mixing a hydrophobic substance with gold and a titanium-containing oxide. Useful methods are, for instance, a method comprising kneading a hydrophobic substance, gold and a titanium-containing oxide, a method comprising kneading a hydrophobic substance and a titanium-containing oxide and immobilizing gold particles on them, etc.

For example, available methods include a method wherein a powdery titanium-containing oxide is made pasty using an organic solvent such as an alcohol, the paste is kneaded together with particles of particulate porous polytetrafluoroethylene (Teflon), the mixture is molded, and gold particles are immobilized on the molded product; a method wherein a powdery hydrophobic silica is kneaded together with a powdery titanium-containing oxide having gold particles immobilized thereon using an organic solvent such as an alcohol, followed by molding; and the like.

The amount of the hydrophobic substance to be used in the second method is about 1 to about 99.9% by weight, preferably about 5 to about 99.5% by weight, more preferably about 10 to about 99% by weight, based on the weight of the finally obtained catalyst.

Process for Partial Oxidation of Unsaturated Hydrocarbon

Described below is a process for preparing an epoxide by partial oxidation of unsaturated hydrocarbon using the catalyst of the present invention.

Unsaturated hydrocarbon having about 2 to about 12 carbon atoms can be used as hydrocarbon, i.e. the raw material. When a reaction is conducted in a gas phase, it is suitable to use as the raw material unsaturated hydrocarbon of about 6 or less carbon atoms such that the reaction product can be easily removed from the catalyst layer even at a low temperature of about 100° C. Specific examples of unsaturated hydrocarbon are compounds having double bonds such as ethylene, propylene, 1-butene, 2-butene, isobutene, 1-pentene, 2-pentene, 2-methyl-1-butene, 3-methyl-1-butene, cyclopentene, 1-hexene, 2-hexene, 3-hexene, 2-methyl-1-pentene, 3-methyl-1-pentene, cyclohexene, 1-methyl-1-cyclopentene, 3-methyl-1-cyclopentene, 4-methyl-1-pentene, etc.

An epoxide can be prepared with a high selectivity by using these unsaturated hydrocarbon as the raw material.

The amount of the catalyst according to the present invention is not particularly limited. From a practical viewpoint, when a reaction is conducted in a gas phase, a suitable amount of the catalyst is within the range which corresponds to a space velocity (SV) in the range of about 100 to about 10000 $hr^{-1} \cdot ml/g \cdot cat$.

In the present invention, the presence of hydrogen is essential. If hydrogen is absent, namely if a mixed gas comprising oxygen, unsaturated hydrocarbon and optionally a diluent gas is reacted in the presence of said catalyst, a reaction is initiated at 200° C. or higher, mainly giving only carbon dioxide but without production of partially oxidized product. On the other hand, when hydrogen is present in the reaction system, a totally different reaction proceeds, affording a partially oxidized product even at a low temperature of about 50° C. The amount of hydrogen to be present is not limited. Usually hydrogen is used in a hydrogen/raw material ratio by volume of about 1/10 to about 100/1 from a practical viewpoint. Generally the larger the proportion of hydrogen is, the higher the reaction rate is. Consequently, it is preferred to select a rather large amount of hydrogen within said range.

The amount of oxygen to be present is not critical. But properly oxygen is present in an oxygen/raw material ratio by volume of about 1/10 to about 10/1. If the amount of oxygen is less than said range, the amount of partially oxidized product is decreased. Hence it is undesirable. On the other hand, if the amount of oxygen is larger than said range, a partially oxidized product is produced not in a correspondingly increased amount but with a lower selectivity (the amount of produced carbon dioxide increases). Hence it is undesirable.

A suitable reaction temperature in the present invention is usually about 0 to about 350° C., preferably about 20 to about 280° C. When a reaction is conducted at a gas phase, it is necessary to select a temperature at which the reaction product shows a sufficient volatility under the specified reaction pressure (usually about 0.01 to about 1 MPa) such that the reaction product is easily removed from the catalyst layer. On the other hand, if an excessively high reaction temperature is used, a burning reaction giving carbon dioxide is likely to occur and at the same time hydrogen is consumed in an increased amount due to its oxidation to water. Hence it is undesirable. While an optimum reaction temperature is variable depending on the raw material to be used, a suitable reaction temperature is presumably in the range of about 20 about 280° C.

A gas phase reaction is conducted under the specified reaction conditions by feeding a mixed gas comprising hydrocarbon, hydrogen, oxygen and optionally a diluent gas (such as nitrogen, argon, helium, carbon dioxide and the like) to a reactor provided with the catalyst of the invention.

A liquid phase reaction is feasible mostly at 100° C. or lower because of non-necessity of removing the reaction product from the catalyst layer. In the liquid phase reaction, a reaction pressure and a reaction temperature are selected from the ranges in which the raw materials can be held liquid, or a reaction is performed by bubbling a mixed gas comprising the raw material, hydrogen, oxygen and optionally a diluent gas in the presence of the catalyst suspended in a solvent (such as benzene and like hydrocarbon solvents, methylene chloride and like halogenated hydrocarbon solvents and the like).

The catalyst of the present invention can exhibit excellent catalytic capability in the presence of oxygen and hydrogen according to reaction conditions inclusive of a reaction temperature, a reaction pressure and the like in a reaction for preparing an epoxide by partial oxidation of unsaturated hydrocarbon. Further the catalyst exhibits little deactivation with time and can stably maintain for a long term its outstanding catalytic capability including a high selectivity and a high activity.

Best Mode for Carrying Out the Invention

The present invention will be described below in more detail with reference to the following Examples.

EXAMPLE 1

A reaction tube having an inner diameter of 20 mm was charged with 10 g of commercially available silica powder (manufactured by Nihon Aerozil Co., Ltd., trade name "AEROZIL 200", 212 m$^2$/g in specific surface area). A He gas containing about 1 vol. % of titanium tetrabutoxide vapor was contacted for about 2 hours at a flow rate of 5000 ml/hr with the silica layer maintained at 80° C., whereby the titanium compound was fixed on the surface of silica. Thereafter the powder was calcined at 600° C. for 3 hours. The obtained powder was mixed with 20 g of commercially available silica sol (manufactured by Nissan Chemical Co., Ltd., trade name "Snowtex N" containing 20% by weight of $SiO_2$) and 200 g of water. Then the mixture was heated to decrease water, giving a paste. The paste was dried at 120° C. for 12 hours and calcined at 600° C. for 3 hours, thereby producing a titania-silica product, i.e. a titanium-silicon composite oxide.

Then, 400 ml of an aqueous solution containing 0.34 g of chloroauric acid ($HAuCl_4$) was heated to 70° C. and was adjusted to a pH of 9.2 with an aqueous solution of sodium hydroxide. Thereafter, 10 g of the titania-silica product obtained above and crushed to 10–20 mesh particles was added to the aqueous solution being stirred, and the mixture was stirred at 70° C. for 30 minutes. The supernatant liquid was removed from the aqueous solution containing said solid. The obtained solid was washed three times with 500 ml of water and filtered. The solid was dried at 120° C. for 12 hours and calcined in air at 400° C. for 3 hours, giving a catalyst comprising a titanium-containing oxide having ultra-fine gold particles supported thereon.

The obtained catalyst had a maximum distribution of gold particles at a particle size of 1 to 3 nm and was found to be a gold-titania-silica catalyst containing 0.05% by weight of ultra-fine gold particles, 0.8% by weight of Ti calculated as $TiO_2$ and 0.14% by weight of Na. The obtained catalyst is hereinafter referred to as "catalyst A".

A reaction tube 10 mm in inner diameter was charged with 2 cc of the obtained gold-titania-silica catalyst A. A He gas containing about 10 vol. % of methoxytrimethylsilane vapor was contacted for about 10 minutes at a flow rate of 5000 ml/hr with the catalyst bed maintained at 200° C. for a silylating treatment, whereby the catalyst was increased in the weight by 2.6% by weight. The catalyst thus silylated is hereinafter referred to as "catalyst B".

The water absorption of the obtained catalyst B was calculated by the following method. 2 g of the catalyst B was dried in air at 170° C. for 2 hours. The weight of the dried catalyst was measured. The catalyst B was left to cool in a desiccator and was allowed to stand at a relative humidity of about 40% and a temperature of about 25° C. for 48 hours. Thereafter the weight of the catalyst containing absorbed water was measured. The water absorption(A) was calculated by the equation shown hereinbefore and was 0.5%.

Subsequently, using the catalyst B, a reaction was conducted for epoxidation of trans-2-butene. Stated more specifically, the catalyst bed containing 2 cc of catalyst B was heated to 210° C. A mixed gas (hydrogen/oxygen/trans-2-butene/argon=20/20/20/40 by vol. ratio) was flowed at a flow rate of 5000 ml/hr. The gas available at an outlet was analyzed to check the change with time in yield from trans-2-butene to 2,3-epoxybutane. The results are shown below in Table 1.

COMPARATIVE EXAMPLE 1

Using the catalyst A obtained in Example 1 and provided before silylation, a reaction was conducted in the same manner as in Example 1 for epoxidation of trans-2-butene. The results are shown below in Table 1.

The water absorption of the catalyst A was calculated in the same manner as in Example 1 and was 1.2%.

TABLE 1

| | Kind of Catalyst | Silylating Treatment | Kind of silylating agent | Yield of 2,3-epoxy butane (%) Lapse of time (hr) | | |
|---|---|---|---|---|---|---|
| | | | | 0.5 | 50 | 150 |
| Ex. 1 | B | Done | Methoxy-trimethyl-silane | 6.3 | 6.0 | 5.8 |
| Comp. Ex. 1 | A | Not done | — | 6.5 | 4.3 | 3.7 |

EXAMPLE 2

A 100 g quantity of commercially available silica (manufactured by Fuji Silysia Chemical Ltd., trade name "Cariact Q-15", 10–20 mesh, a specific surface area 196 m$^2$/g) was added to 400 ml of water containing 7.4 g of a 50 wt % aqueous solution of titanium bisammonium lactate dihydroxide (manufactured by Aldrich Co., Ltd.). After immersion therein for about 10 minutes, water was distilled off under reduced pressure and the residue was dried at 120° C. for 12 hours. Then it was calcined at 900° C. for 3 hours to give a titanium/silicon composite oxide (titania-silica product).

Subsequently 900 ml of an aqueous solution containing 0.34 g of chloroauric acid (HAuCl$_4$) was heated to 70° C. and was adjusted to a pH of 9.5 with an aqueous solution of sodium hydroxide. Thereafter, 20 g of the titania-silica product obtained above was added to the aqueous solution being stirred, and the mixture was stirred at 65° C. for 30 minutes. The supernatant liquid was removed from the aqueous solution containing said solid. The obtained solid was washed three times with 1000 ml of water and filtered. The solid was added to 200 ml of an aqueous solution containing 0.99 g of cesium carbonate and water was distilled off under reduced pressure. The residue was dried at 120° C. for 12 hours and calcined in air at 400° C. for 3 hours, giving a catalyst comprising a titanium-containing oxide having ultra-fine gold particles supported thereon.

The obtained catalyst had a maximum distribution of gold particles at a particle size of 1 to 3 nm and was found to be a gold-titania-silica catalyst containing 0.1% by weight of ultra-fine gold particles, 1.0% by weight of Ti calculated as TiO$_2$, 0.09% by weight of Na and 0.4% by weight of Cs. The obtained catalyst is hereinafter referred to as "catalyst C".

Thereafter 10 cc of the obtained gold-titania-silica catalyst C was mixed with 1 g of 1,1,1,3,3,3-hexamethyldisilazane and 50 cc of toluene. Then the mixture was stirred with heating at 150° C. for 1 hour under increased pressure. After the mixture was filtered, the solid was washed with toluene and was vacuum-dried at 100° C. and 10 mmHg. The solid was given a 3.6 wt % increased weight by the silylating treatment. The thus silylated catalyst is hereinafter referred to as "catalyst D".

A reaction tube 10 mm in inner diameter was charged with 2 cc of the obtained catalyst D. A mixed gas (hydrogen/oxygen/propylene/argon=20/20/8/52 by vol. ratio) was flowed at a flow rate of 5000 ml/hr through the catalyst bed maintained at 185° C. The gas available at an outlet was analyzed to check the change with time in yield from propylene to propylene oxide. The results are shown below in Table 2.

The water absorption of the catalyst D was calculated in the same manner as in Example 1 and was 0.4%.

COMPARATIVE EXAMPLE 2

Using the catalyst C obtained in Example 2 and provided before silylation, a reaction was conducted in the same manner as in Example 2 for epoxidation from propylene to propylene oxide. The results are shown below in Table 2.

The water absorption of the catalyst C was calculated in the same manner as in Example 1 and was 1.7%.

TABLE 2

| | Kind of Catalyst | Silylating Treatment | Kind of silylating agent | Yield of propylene oxide (%) Lapse of time (hr) | | |
|---|---|---|---|---|---|---|
| | | | | 0.5 | 50 | 150 |
| Ex. 2 | D | Done | 1,1,1,3,3,3-Hexa-methyldi-silazane | 4.2 | 4.1 | 4.0 |
| Comp. Ex. 1 | C | Not done | — | 4.4 | 2.9 | 2.4 |

It is apparent from the results shown above that the catalyst of the present invention can stably act for a long term in a reaction for partial oxidation of unsaturated hydrocarbon.

EXAMPLE 3

A 200 g quantity of commercially available silica (manufactured by Fuji Silysia Chemical Ltd., trade name "Cariact Q-10", 10–20 mesh, a specific surface area 326 m$^2$/g) was added to a solution of 3.6 g of tetraisopropyl titanate and 5.0 g of acetylacetone in 300 ml of methyl alcohol and was immersed therein for 10 minutes. The methyl alcohol was distilled off under reduced pressure. The residue was dried at 120° C. for 12 hours. Then it was calcined at 900° C. for 3 hours to give a titanium-silicon composite oxide (titania-silica product).

Subsequently 900 ml of an aqueous solution containing 0.34 g of chloroauric acid (HAuCl$_4$) was heated to 70° C. and was adjusted to a pH of 9.5 with an aqueous solution of potassium hydroxide. Thereafter, 20 g of the titania-silica product obtained above was added to the aqueous solution being stirred, and the mixture was stirred at 70° C. for 30 minutes. The supernatant liquid was removed from the aqueous solution containing said solid. The obtained solid was washed three times with 1000 ml of water and filtered. The solid was dried at 120° C. for 12 hours and calcined in air at 400° C. for 3 hours, giving a catalyst comprising a titanium-containing oxide having ultra-fine gold particles supported thereon. The obtained catalyst had a maximum distribution of gold particles at a particle size of 1 to 3 nm and was found to be a gold-titania-silica catalyst containing 0.04% by weight of ultra-fine gold particles, 0.5% by weight of Ti calculated as TiO$_2$, and 0.18% by weight of K. The obtained catalyst is hereinafter referred to as "catalyst E".

Then, 2 cc of the obtained gold-titania-silica catalyst E was placed into a reaction tube made of stainless steel and 10 mm in inner diameter. A He gas containing about 10 vol. % of methoxytrimethylsilane vapor was contacted for about 10 minutes at a flow rate of 5000 ml/hr with the catalyst bed maintained at 200° C. for a silylating treatment, whereby the catalyst was increased in the weight by 2.3% by weight. The catalyst thus silylated is hereinafter referred to as "catalyst F".

Using the catalyst F obtained above, a reaction was conducted for epoxidation from propylene to propylene oxide. Stated more specifically, the catalyst bed containing 2 cc of the catalyst F was heated to the reaction temperature shown below in Table 3. At the pressure shown below in Table 3, a mixed gas (hydrogen/oxygen/propylene/argon= 20/20/20/40 by vol. ratio) was flowed at a flow rate of 5000 ml/hr. The gas available at an outlet was analyzed to check the changes with time in yield from propylene to propylene oxide and in hydrogen conversion. The results are shown below in Table 3.

The water absorption of the catalyst F was calculated in the same manner as in Example 1 and was 0.7%.

COMPARATIVE EXAMPLE 3

Using the catalyst E obtained in Example 3 and provided before silylation, a reaction was conducted in the same manner as in Example 3 for epoxidation from propylene to propylene oxide. The results are shown below in Table 3.

The water absorption of the catalyst E was calculated in the same manner as in Example 1 and was 1.4%.

gas(hydrogen/oxygen/propylene/argon=20/20/20/40 by vol. ratio) was flowed at a flow rate of 5000 ml/hr. The gas flowing at an outlet was analyzed to check the changes with time in yield from propylene to propylene oxide and in hydrogen conversion. The results are shown below in Table 4.

The water absorption of the catalyst H was calculated in the same manner as in Example 1 and was 0.6%.

COMPARATIVE EXAMPLE 4

Using the catalyst G obtained in Example 4, a reaction was conducted in the same manner as in Example 4 for epoxidation from propylene to propylene oxide. The results are shown below in Table 4.

The water absorption of the catalyst G was calculated in the same manner as in Example 1 and was 0.8%.

TABLE 3

| Lapse of time after start of reaction (hr) | Reaction temperature (° C.) | Pressure | Example 3 Catalyst F | | Comp. Example 3 Catalyst E | |
|---|---|---|---|---|---|---|
| | | | Yield of propylene oxide (%) | Conversion of hydrogen (%) | Yield of propylene oxide (%) | Conversion of hydrogen (%) |
| 2 | 190 | Atms. pres. | 2.6 | 10.3 | 2.8 | 9.2 |
| 4 | 200 | Atms. pres. | 3.0 | 13.2 | 3.2 | 12.3 |
| 6 | 210 | Atms. pres. | 3.8 | 16.4 | 2.9 | 14.1 |
| 8 | 210 | 0.1 MPa (gauge pressure) | 5.0 | 22.2 | 3.4 | 20.1 |
| 10 | 210 | 0.2 MPa (gauge pressure) | 5.5 | 24.6 | 3.1 | 22.7 |

Note: Atms. pres. = atmospheric pressure

It is apparent from the above results that the catalyst of the present invention, even when continuously used for a long term, can effectively exhibit excellent catalytic capability according to the reaction conditions. On the other hand, the catalyst E used in Comparative Example 3 was degraded in catalytic capability when continuously used for a long term and, when used under varied reaction conditions, can not effectively exhibit catalytic capability according to the reaction conditions.

EXAMPLE 4

A gold-titania-silica catalyst was prepared in the same manner as in Example 3 except that 7.2 g of tetraisopropyl titanate was used and the titania-silica product was calcined at 600° C. The obtained catalyst is hereinafter referred to as "catalyst G".

A fluorescent X-ray analysis shows that the catalyst G contains 0.21% by weight of Au, 1.09% by weight of Ti calculated as $TiO_2$, and 0.22% by weight of K.

A fluorine-containing resin was sprayed twice over 10 g of catalyst G using a spray containing a fluorine-containing resin (produced by Sumitomo 3M Co., Ltd, trade name "CAT. No. SG-SX Tent"). The coated catalyst was heat-treated in air at 200° C. for 2 hours. The catalyst obtained above is hereinafter referred to as "catalyst H".

Using 2 cc of the catalyst H obtained above, a reaction was conducted for epoxidation from propylene to propylene oxide. Stated more specifically, the catalyst bed containing 2 cc of the catalyst H was heated to 170° C. A mixed

TABLE 4

| Lapse of time after start of reaction (hr) | Example 4 Catalyst H Yield of propylene oxide (%) | Comp. Example 4 Catalyst G Yield of propylene oxide (%) |
|---|---|---|
| 1 | 2.10 | 3.23 |
| 5 | 2.09 | 2.50 |
| 10 | 2.11 | 1.90 |
| 50 | 2.13 | 1.40 |

EXAMPLE 5

A 300 g quantity of commercially available silica (manufactured by Fuji Silysia Chemical Ltd., trade name "Cariact Q-10", 10–20 mexh) was added to a solution of 6.56 g of titanylacetyl acetonate in 650 ml of methanol. The methanol was distilled off under atmospheric pressure. The residue was dried at 120° C. for 12 hours. Then it was calcined at 800° C. for 3 hours to give a titania-silica (Ti—$SiO_2$) product.

Subsequently 25 g of the titania-silica (Ti—$SiO_2$) product was immersed in 50 ml of an aqueous solution of 0.33 g of magnesium nitrate-hexahydrate and heated to distill off water. The residue was dried at 120° C. for 12 hours. Then it was calcined at 800° C. for 3 hours to give a titania-silica product modified by magnesium (Mg—Ti—$SiO_2$).

Then, the magnesium-modified titania-silica product was caused to support ultra-fine gold particles thereon by the same method as in Example 1, giving a gold-titania-silica product modified by magnesium (Au—Mg—Ti—SiO$_2$). The obtained product is hereinafter referred to as "catalyst G".

Subsequently 2 cc of the catalyst G was added to 5 cc of a toluene solution containing 0.01 g of trimethylmethoxysilane serving as a silylating agent. The mixture was heated at 50° C. for 30 minutes in a closed container. Then, toluene was distilled off to silylate the catalyst G.

The catalyst silylated in this way was filled into a reaction tube 10 mm in inner diameter. Then, an Ar gas was passed through the reaction tube maintained at 220° C. in an oil bath at a flow rate of 5000 ml/hr for 30 minutes. A mixed gas (hydrogen/oxygen/propylene/argon=20/20/20/40 by vol. ratio) was flowed at a flow rate of 5000 ml/hr. The gas flowing at an outlet was analyzed to check the change with time in yield from propylene to propylene oxide. The results are shown below in Table 5.

EXAMPLE 6

The catalyst G was subjected to a silylating treatment in the same manner as in Example 5 with the exception of using dimethyldimethoxysilane in place of trimethylmethoxysilane. Using said catalyst, a reaction was conducted for epoxidation from propylene to propylene oxide in the same manner as in Example 5. The change with time in yield of propylene oxide was checked. The results are shown below in Table 5.

EXAMPLE 7

The catalyst G was subjected to a silylating treatment in the same manner as in Example 5 with the exception of using diphenyldimethoxysilane in place of trimethylmethoxysilane. Using said catalyst, a reaction was conducted for epoxidation from propylene to propylene oxide in the same manner as in Example 5. The change with time in yield of propylene oxide was checked. The results are shown below in Table 5.

EXAMPLE 8

The catalyst G was subjected to a silylating treatment in the same manner as in Example 5 with the exception of using phenyltrimethoxysilane in place of trimethylmethoxysilane. Using said catalyst, a reaction was conducted for epoxidation from propylene to propylene oxide in the same manner as in Example 5. The change in yield of propylene oxide with time was checked. The results are shown below in Table 5.

COMPARATIVE EXAMPLE 4

Using the catalyst G obtained in Example 5, a reaction was conducted, without silylation, for epoxidation from propylene to propylene oxide in the same manner as in Example 5. The change in yield of propylene oxide with time was checked. The results are shown below in Table 5.

TABLE 5

| | Kind of silylating agent | Yield of propylene oxide (%) | |
|---|---|---|---|
| | | 1 hour after start of reaction | 100 hours after start of reaction |
| Example 5 | Trimethyl-Methoxysilane | 4.3 | 3.4 |
| Example 6 | Dimethyldi-Methoxysilane | 4.1 | 3.3 |
| Example 7 | Diphenyldi-Methoxysilane | 4.1 | 3.4 |

TABLE 5-continued

| | Kind of silylating agent | Yield of propylene oxide (%) | |
|---|---|---|---|
| | | 1 hour after start of reaction | 100 hours after start of reaction |
| Example 8 | Phenyltri-Methoxysilane | 3.9 | 3.2 |
| Comp. Example 4 | None | 2.6 | 2.1 |

EXAMPLE 9

A 200 g quantity of commercially available silica (manufactured by Fuji Silysia Chemical Ltd., trade name "Cariact Q-30", 10–20 mesh, a specific surface area 103 m$^2$/g) was added to 400 ml of a solution of 4.4 g of tetraisopropyl titanate and 3.3 g of acetylacetone in isopropanol. The mixture was stirred for 1 hour, and filtered. The obtained solid was washed twice with 400 ml of isopropanol. It was dried at 120° C. for 12 hours and was calcined at 900° C. for 3 hours to give a titania-silica product.

Subsequently 300 ml of an aqueous solution containing 0.026 g of chloroauric acid and 0.15 g of sodium laurate was adjusted to a pH of 8 with an aqueous solution of sodium hydroxide while being maintained at 70° C. Thereafter, 20 g of the titania-silica product obtained above was added to the solution, and the mixture was stirred for 30 minutes while the pH was maintained at 7–8. The supernatant liquid was removed from the aqueous solution. The obtained solid was washed three times with 300 ml of water and filtered. The solid was dried at 120° C. for 10 hours and calcined at 300° C. for 3 hours, giving a gold-titania-silica product. The obtained product is hereinafter referred to as "catalyst H".

Then, 2 cc of the catalyst H was placed into a reaction tube 10 mm in inner diameter. While maintaining the catalyst bed at 160° C. in an electric furnace, an Ar gas containing about 5 vol. % of trimethylmethoxysilane vapor was passed at a flow rate of 6000 ml/hr for 5 minutes for silylating treatment. Thereafter the reaction tube was immersed in an oil bath at 220° C. A mixed gas (hydrogen/oxygen/propylene/argon=20/20/20/40 by vol. ratio) was flowed at a flow rate of 5000 ml/hr. The gas available at an outlet was analyzed to check the change with time in yield from propylene to propylene oxide. The results are shown below in Table 6.

EXAMPLE 10

The catalyst H was subjected to a silylating treatment in the same manner as in Example 9 except that the catalyst bed was held at a temperature of 220° C. in silylation of the catalyst H. Using this catalyst, a reaction was conducted for epoxidation from propylene to propylene oxide in the same manner as in Example 9. The change with time in yield from propylene to propylene oxide was checked. The results are shown below in Table 6.

EXAMPLE 11

The catalyst H was subjected to a silylating treatment in the same manner as in Example 9 except that the catalyst bed was held at a temperature of 280° C. in silylation of the catalyst H. Using this catalyst, a reaction was conducted for epoxidation from propylene to propylene oxide in the same manner as in Example 9. The change with time in yield of propylene oxide was checked. The results are shown below in Table 6.

COMPARATIVE EXAMPLE 5

Using the catalyst H obtained in Example 9, a reaction was conducted, without silylation, for epoxidation from propylene to propylene oxide in the same manner as in Example 9. The change with time in yield of propylene oxide was checked. The results are shown below in Table 6.

TABLE 6

| | Yield of propylene oxide (%) | |
|---|---|---|
| | 1 hour after start of reaction | 5 hours after start of reaction |
| Example 9 | 4.3 | 4.0 |
| Example 10 | 4.1 | 3.8 |
| Example 11 | 4.0 | 3.8 |
| Comp. Example 5 | 3.1 | 2.1 |

EXAMPLE 12

The catalyst H was subjected to a silylating treatment in the same manner as in Example 9 except that the catalyst bed was held at a temperature of 280° C. in silylation of the catalyst H and that an Ar gas containing about 9 vol. % of trimethylmethoxysilane vapor was passed at a flow rate of 6000 ml/hr for 15 minutes to contact the catalyst H with the vapor.

The change with time in yield from propylene to propylene oxide was checked in the same manner as in Example 9 with the exception of using a reaction tube filled with the catalyst silylated in the above manner, and conducting a reaction at an oil bath temperature of 200° C. and a pressure of 2 kg/cm²·G for epoxidation from propylene to propylene oxide. The results are shown below in Table 7. A molar ratio of the amount of consumed hydrogen to the amount of propylene oxide produced 50 hours after start of reaction was 2.7:1.

EXAMPLE 13

The catalyst H was subjected to a silylating treatment in the same manner as in Example 9 except that the catalyst bed was held at a temperature of 280° C. in silylation of the catalyst H and that an Ar gas containing about 9 vol. % of trimethylmethoxysilane vapor was passed at a flow rate of 6000 ml/hr for 40 minutes to contact the catalyst H with the vapor.

The change with time in yield from propylene to propylene oxide was checked in the same manner as in Example 9 except that using a reaction tube filled with the catalyst silylated in the above manner, a reaction was conducted at an oil bath temperature of 200° C. and a pressure of 5 kg/cm²·G for epoxidation of propylene. The results are shown below in Table 7. A molar ratio of the amount of consumed hydrogen to the amount of propylene oxide produced 50 hours after start of reaction was 2.9:1.

COMPARATIVE EXAMPLE 6

Using the catalyst H obtained in Example 9, a reaction was conducted, without silylation, for epoxidation from propylene to propylene oxide in the same manner as in Example 13. The change with time in yield of propylene oxide was checked. The results are shown below in Table 7. A molar ratio of the amount of consumed hydrogen to the amount of propylene oxide produced 50 hours after start of reaction was 4.0:1.

TABLE 7

| | Yield of propylene oxide (%) | |
|---|---|---|
| | 1 hour after start of reaction | 50 hours after start of reaction |
| Example 12 | 5.6 | 4.5 |
| Example 13 | 4.9 | 4.3 |
| Comp. Example 6 | 3.2 | 1.8 |

EXAMPLE 14

A gold-titania-silica product was prepared in the same manner as in Example 9 with the exception of using commercially available silica (manufactured by Fuji Silysia Chemical Ltd., trade name "Cariact Q-30", 10–20 mesh, a specific surface area 79 m²/g) in place of the silica used in Example 9. The obtained product is hereinafter referred to as "catalyst I".

The catalyst I (2 cc) was filled into a reaction tube 10 mm in inner diameter. While maintaining the catalyst bed at 280° C. in an electric furnace, an Ar gas containing about 9 vol. % of trimethoxysilane vapor was passed at a flow rate of 6000 ml/hr for 30 minutes for a silylating treatment. The reaction tube was immersed in an oil bath at 200° C. and a mixed gas (hydrogen/oxygen/propylene/argon=8/8/25/59 by vol.ratio) was flowed under a pressure of 8 kg/cm²·G at a flow rate of 6000 ml/hr (flow rate as measured at an ambient pressure and temperature). The gas available at an outlet was analyzed to check the change with time in yield from propylene to propylene oxide. The results are shown below in Table 8. A molar ratio of the amount of consumed hydrogen to the amount of propylene oxide produced 50 hours after start of reaction was 2.8:1.

COMPARATIVE EXAMPLE 7

Using the catalyst I, a reaction was conducted, without silylation, for epoxidation from propylene to propylene oxide in the same manner as in Example 14. The change with time in yield of propylene oxide was checked. The results are shown below in Table 8. A molar ratio of the amount of consumed hydrogen to the amount of propylene oxide produced 50 hours after start of reaction was 4.8:1.

TABLE 8

| | Yield of propylene oxide (%) | |
|---|---|---|
| | 1 hour after start of reaction | 50 hours after start of reaction |
| Example 14 | 4.6 | 4.3 |
| Comp. Example 7 | 3.1 | 1.6 |

What is claimed is:

1. A catalyst for partial oxidation of unsaturated hydrocarbon, characterized in that the catalyst comprises finely divided gold particles immobilized on a titanium-containing oxide and is one subjected to a silylating treatment.

2. A catalyst for partial oxidation of unsaturated hydrocarbon, characterized in that the catalyst comprises finely divided gold particles immobilized on a titanium-containing oxide and is one subjected to a hydrophobilizing treatment.

3. The catalyst according to claim 2, wherein the hydrophobilizing treatment is conducted using at least one hydrophobilizing agent selected from the group consisting of organic fluorinating agents and silylating agents.

4. The catalyst according to claim 1 or 2, wherein the finely divided gold particles are ultra-fine particles having a particle size of 10 nm or less.

5. The catalyst according to claim 1 or 2, wherein the titanium-containing oxide is at least one member selected from the group consisting of titanium oxides, titanates, oxide mixtures of titanium oxide and silicon-containing oxide physically mixed together, and composite oxides prepared by chemically bonding titanium and silicon via oxygen.

6. The catalyst according to claim 1 or 2, wherein the titanium-containing oxide contains at least one element selected from the group consisting of alkali metals, alkaline earth metals, lanthanoids and thallium.

7. The catalyst according to claim 1, wherein the silylating treatment is carried out by bringing the titanium-containing oxide into contact with a silylating agent at a temperature of 450° C. or lower before or after immobilizing the finely divided gold on the titanium-containing oxide.

8. The catalyst according to claim 2, wherein the hydrophobilizing treatment is carried out by bringing the titanium-containing oxide into contact with a hydrophobilizing agent at a temperature of 450° C. or lower before or after immobilizing the finely divided gold on the titanium-containing oxide.

9. A process for preparing an epoxide, comprising the step of partially oxidizing unsaturated hydrocarbon with oxygen in the presence of the catalyst as defined in any of claim 1, 2, 3, 7 or 8 and molecular hydrogen.

10. A process for preparing an epoxide, comprising the step of partially oxidizing unsaturated hydrocarbon with oxygen in the presence of the catalyst as defined in claim 4 and molecular hydrogen.

11. A process for preparing an epoxide, comprising the step of partially oxidizing unsaturated hydrocarbon with oxygen in the presence of the catalyst as defined in claim 5 and molecular hydrogen.

12. A process for preparing an epoxide, comprising the step of partially oxidizing unsaturated hydrocarbon with oxygen in the presence of the catalyst as defined in claim 6 and molecular hydrogen.

* * * * *